(12) United States Patent
Chevillon et al.

(10) Patent No.: US 6,342,059 B1
(45) Date of Patent: Jan. 29, 2002

(54) MEDICAL TREATMENT OF AN AFFECTION OF AN ANATOMICAL DUCT

(75) Inventors: Gérard Chevillon, Montrouge; Guy Nadal, Poitiers; Samy Anidjar, Paris, all of (FR)

(73) Assignee: B. Braun Celsa, Boulogne-Billancourt (FR)

( * ) Notice: Subject to any disclaimer, the term of this patent is extended or adjusted under 35 U.S.C. 154(b) by 0 days.

(21) Appl. No.: 09/722,682

(22) Filed: Nov. 28, 2000

Related U.S. Application Data (62) Division of application No. 09/355,879, filed on Oct. 20, 1999, now Pat. No. 6,248,116.

(30) Foreign Application Priority Data

Dec. 16, 1997 (FR) .............................................. 97 15969
Dec. 29, 1997 (FR) .............................................. 97 16625

(51) Int. Cl.⁷ .............................................. A61B 17/00
(52) U.S. Cl. ..................................................... 606/139
(58) Field of Search .............................. 606/139, 142, 606/151, 143, 144, 213, 140, 153–156; 623/1.36, 1.13, 1.14

(56) References Cited

U.S. PATENT DOCUMENTS

| | | |
|---|---|---|
| 4,733,665 A | 3/1988 | Palmaz |
| 5,246,156 A | 9/1993 | Rothfuss et al. |
| 5,333,772 A | 8/1994 | Rothfuss et al. |
| 5,470,010 A | 11/1995 | Rothfuss et al. |
| 5,527,355 A * | 6/1996 | Ahn .......................... 623/1.36 |
| 5,707,378 A | 1/1998 | Ahn et al. ................... 606/139 |
| 5,972,003 A | 10/1999 | Rousseau et al. ........... 606/139 |
| 6,004,347 A * | 12/1999 | McNamara et al. ........ 623/1.13 |
| 6,039,753 A | 3/2000 | Meislin ....................... 606/213 |

FOREIGN PATENT DOCUMENTS

| | | |
|---|---|---|
| EP | 90/15582 | 12/1990 |
| EP | 541987 | 5/1993 |
| EP | 579523 | 1/1994 |
| EP | 688544 | 12/1995 |
| FR | 2737404 | 2/1997 |
| FR | 2746292 | 9/1997 |
| FR | 2773057 | 7/1999 |
| GB | 2269104 | 2/1994 |
| WO | 96/07371 | 3/1996 |
| WO | 9709008 | 3/1997 |
| WO | 97/19653 | 6/1997 |
| WO | 9739687 | 10/1997 |
| WO | 9741804 | 11/1997 |

* cited by examiner

Primary Examiner—Kevin Truong
(74) Attorney, Agent, or Firm—Rothwell, Figg, Ersnt & Manbeck, P.C.

(57) ABSTRACT

This invention relates to a medical device comprising an implant for the treatment of an affection of an anatomical duct. A part of the duct (V) wall is lined on the outside with at least one lining (140′a), essentially facing the proximal and/or distal ends of the implant (100). Means of fastening (361) the lining to the implant apply, through the duct wall, the implant against this duct, and means of setting both the lining and the fastening means allow their positioning around said duct. In particular, application to the treatment of an aneurysm.

7 Claims, 8 Drawing Sheets

FIG_1

FIG_5

FIG_9

FIG_10

FIG. 6

FIG_7

FIG_8

FIG_12

MEDICAL TREATMENT OF AN AFFECTION OF AN ANATOMICAL DUCT

This application is a division of Ser. No. 09/355,879, filed Oct. 20, 1999, now U.S. Pat. No. 6,248,116.

This invention relates to a medical unit or device aimed at improving the conditions of the setting and holding of an implant in an anatomical duct, particularly in the case of a vascular implant or endoprosthesis for aneurysm that must be set at least partly by percutaneous endoluminal access.

Various types of implants and various techniques for setting them are already known.

For instance, the U.S. Pat. No. 5,527,355 or 5,707,378 show a device and a method for treating aneurysms through the fitting of a strap around the vessel outer surface, where spring-like means are used to hold the implant against the vessel (stents).

Is thus known a medical unit for the treatment of an affection of an anatomical duct, comprising:

an implant that can be introduced in the duct to be treated, the implant having a general axis and presenting, substantially along said axis, two free ends, respectively proximal and distal, at least one lining, to at least partly line the outer duct wall, essentially opposite the proximal end of the implant, and means for fastening the lining to the implant, through the duct wall, so as to hold internally the implant against the duct wall.

According to these patents, as many as two lining straps have been provided on both proximal and distal ends of the implant, which is itself designed so as to be introduced in a radially restrained state. Thereafter, it expands radially to treat the aneurysm.

Nonetheless, some problems remain, related to the conditions under which the strap is set around the given duct and the implant is fastened to this duct wall, as well as to the possible fluidtight conditions required vis-à-vis the circulating fluid.

It will be noted that, in the aforementioned patents, the method used to fasten each strap around the duct can cause a problem, especially if the aorta is concerned, since it can be particularly difficult to try to completely surround it.

Moreover, the physician may find it difficult to succeed in positioning the lining strap exactly across from the corresponding end of the implant, which nonetheless must be done to insure an adequate fastening between them. This fastening is indeed achieved by the hooks connected to one of the implant stents.

The way in which this invention solves the problem consists in particular in providing a medical unit that also includes means of setting the fastening elements, which are distinct from the implant, so as to preferably install these fastening means from the outside of the duct, toward the implant.

Hence the implant fastening hooks are not used to bind together the lining, the duct and the implant. Moreover, according to the invention, the implant could be devoid of any fastening hook to anchor it in the duct Approaching the duct from the outside appears to be technically the least dangerous so far for the patient, all the more so if, as otherwise suggested, the fastening between lining strap(s) and implant is performed, through the duct, by means of surgical staples set in place by a surgical stapler designed to introduce and curve the free ends of each staple from only one side of the given duct An endoscopic (or laparoscopic) approach is proposed.

It is to be noted that these "staplers," including the endoscopic staplers (such as the one from ETHICON© in U.S. Pat. No. 5,470,010 or 5,333,772), have not been designed so far to staple through a duct where a fluid circulates (such as a blood vessel), because of possible leaks due to the perforation caused by the staple. It is thus an application that is uncommon to date and goes against the current instructions for the use of such an equipment It should also be noted that the choice of both the stapler and the staple is of great significance. A cutaneous stapler (such as a stapler like ROYAL® from the firm AUTOSUTURE) seems unsuitable in that the staple is initially lying flat, until the stapler closes it progressively to a shape in "⊂⊐" by driving it forward and then closing in its free ends. What is a priori an effective way to draw together two lips of a cut does not seem appropriate to a fastening through an internal duct containing body fluids, a fragile vessel especially.

In this respect, an important characteristic of this invention consists in recommending that the staples be, when first introduced (hence before the stapler acts to distort them) in the shape of a "Π" so that they go through the lining, the duct and the implant. Then in a second step (after they go through the lining, the duct and the implant), the stapler will bring them substantially to the shape of a "⊏⊐"

More broadly, and even if fastening means other than staples are used, such as the rivets described in FR 97 16625, another important characteristic of the invention is the recommendation that these fastening means consist in means of tightening that have, parallel to their introduction axis (through the aforementioned layers), a difference in length between the initial stage of introduction through the outer lining, the duct and the implant, and a second fastening stage after this introduction, so as to tightly pinch the duct wall between the outer lining and the inner implant, thus insuring fluidtightness between the implant and the wall of said duct vis-à-vis the fluid that circulates in the duct.

The (each) lining can be in the form of a local pad placed in the same area as the fastening means or, even better, as a split strap or collar at the periphery of the duct.

To insure a "soft" yet uniform enough contact between the lining and the duct, the preferred lining will present a frame covered (at least on the inside) by a damping pad.

So as to better hold it in place at the time of its fastening and thereafter, the preferred lining will be mechanically resistant in the sense of its thickness, in such a way as to constitute a support for the fastening means.

And, to promote a lasting hold, the lining can include an "adhesive" layer (favorable to cellular development and designed to come in contact with the anatomical duct).

Since not all anatomical ducts have the same section and since a same duct can also display different sections for different persons, this invention also provides that, in the case of a strap (or open collar), the preferred lining will originally have a length superior to the duct circumference that can be trimmed later to be adjusted to the duct section.

An added characteristic of this invention provides that the lining be fit to be pierced, or be structurally designed, with openings (preferably self-obturating openings) to allow the fastening means to pass therethrough thus easing such a passage.

A further aspect of the invention relates to the way of implanting and using the medical unit aforedescribed (see the enclosed <<method claims>> 14 to 17).

The invention will be seen more in detail in the following description and attached drawings in which.

In the following description, is only taken into consideration the case of an implant consisting of an endoprosthesis for the treatment of an aneurysm of the aorta even though other vessels, or other kinds of affections, can benefit from the improvements provided by the invention.

Figure 1:
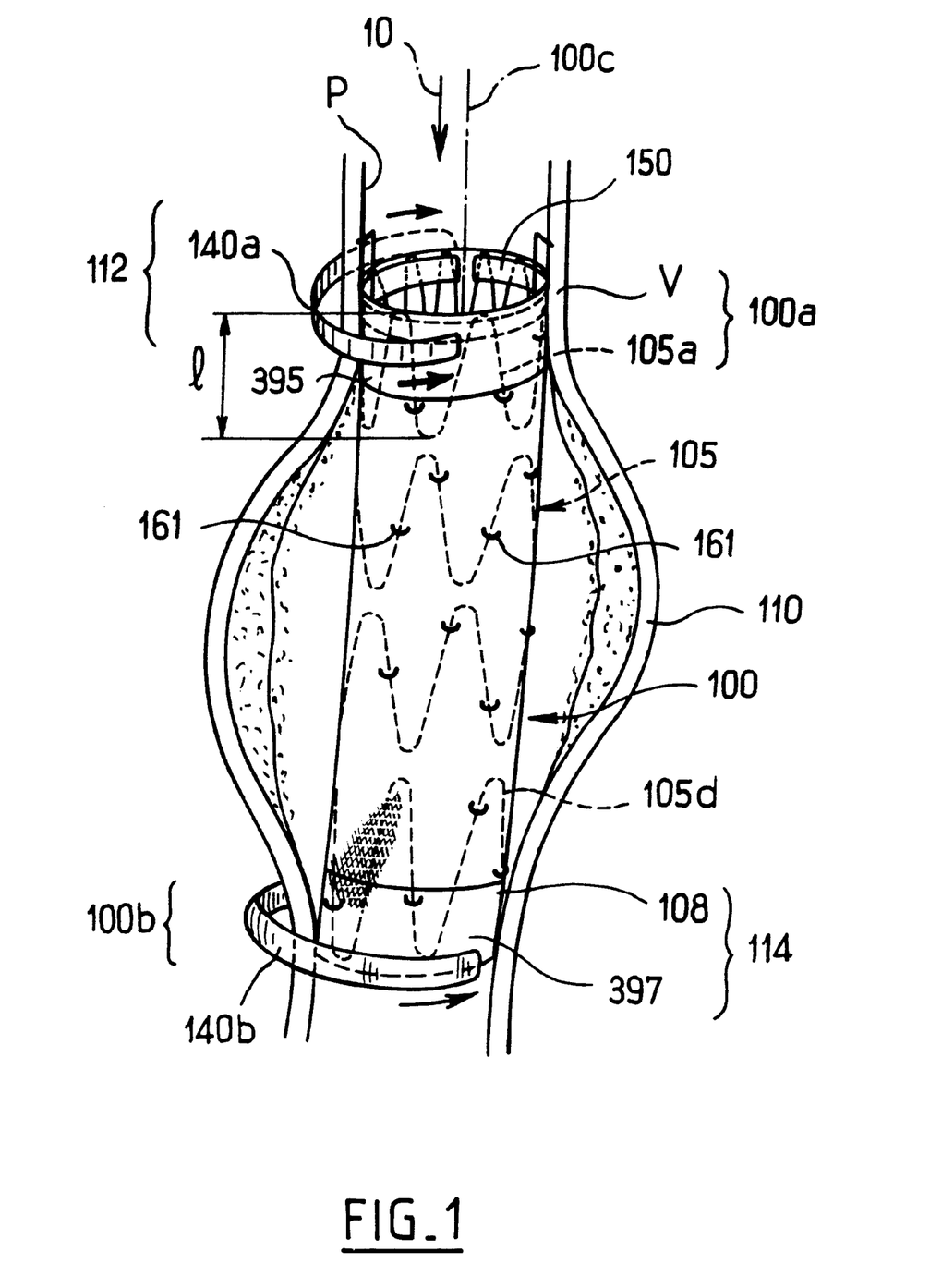
FIG. 1 shows the implant set in an aortic aneurysm with two lining straps ready to go around it.

FIG. 1 thus shows an aorta V with an aneurysm 110. The aneurysm is circumscribed by an upper (upstream) neck 112 and a lower (downstream) neck 114. The direction of the bloodstream is as shown in 10.

An endoprosthesis 100, with its axis 100c, is implanted at least in the area of the aneurysm.

The implant 100 may in particular be such as described in U.S. Pat. No. 4,533,665, or in FR-A-2 732 404.

The implant is pressed, near its proximal end 100a, against the wall P of the vessel V, by means of at least one stretching element 105, radially expansible and usually called "stent".

In addition to the stent 105 (consisting here of four tiers or levels of wire threads running zigzag and coiled onto themselves at each tier), the implant 100 comprises a supple sleeve 108, made of synthetic and biocompatible material such as Dacron (registered trademark), acting as a channel for the bloodstream, once the prosthesis is implanted. Each elementary stent is stitched to the sheath in 161. An elementary stent is found near the two free ends 100a and 100b of the implant.

The (each) stent 105 is radially "self-expansible" (as shown in FR-A-2 732 404), although it could also consist of a perforated metal tube, radially expansible beyond its elastic yield when subjected to an inner radial expansion force such as a balloon, as in U.S. Pat. No. 4,533,665.

Since the tight affixing of the implant against the higher and lower necks is carried out by the first and last levels 105a, 105d of the stent, these levels can present a radial force (or a resistance to radial compression) higher than at the other levels and/or the rest of the implant. This mechanical effect can be obtained, for instance, by increasing the number of zigzags at the first level and/or by decreasing the axial length l of these levels compared with the other levels of the stent. Yet another solution could be to insert an additional means of reinforcement such as, for instance, a split ring 150.

Around the duct V, and more particularly around the highest and lowest necks, a strap 140a, 140b is designed to line the duct.

Once in place, the strap will come to line locally the vessel wall so as to promote the setting of the fastening means of each strap to the implant 100, through the duct V wall, to affix on the inside this implant against the wall P, preferably in a bloodtight way.

The strap may be implemented in several appropriate ways.

If each strap is resistant enough to crushing in the sense of its thickness (as referenced in e in the FIG. 2), the strap will advantageously form an outer support for the fastening means, while the implant 100 itself can form the inner support, by means of the stent 105, or of a strap, a local pad or an additional split ring referenced 150 in FIG. 1 and fastened near the proximal end of the implant to support it.

Figure 2:
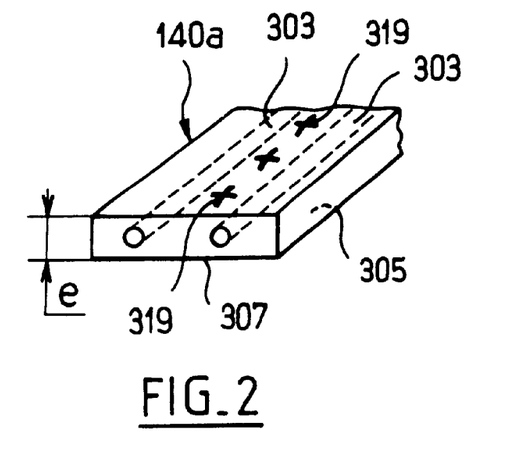
FIG. 2 shows an enlarged view in perspective of a possible implementation of one of these straps.

In FIG. 2, the lining element appears as a strap containing one or more metal or plastic wires (303) (here, two parallel wires) embedded in a damping pad 305 (made of felt, for instance), the whole possibly coated with a thin envelop 307, in Dacron (registered trademark) for instance.

Figure 3:
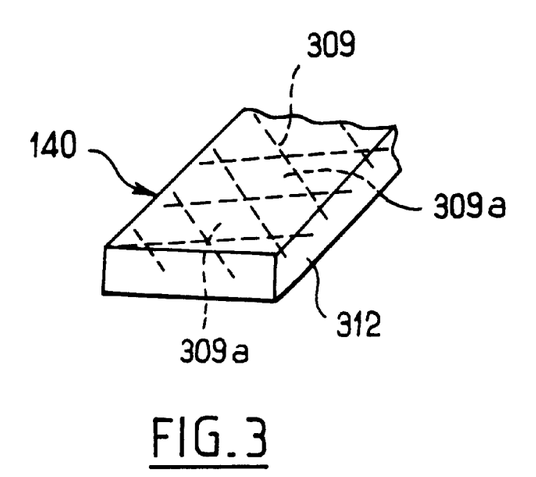
FIG. 3 is a variation on the implementation of a strap viewed as in FIG. 2.

In FIG. 3, the strap 140 comprises a somewhat rigid lattice 309, embedded in a protective layer 312 to damp the contact with the vessel. The layer 312 could be set only on the inside where the strap comes in contact with the vessel, the supporting frame 309 being thus on the surface.

In another variation not represented, the strap could be implemented as a felt pad reinforced with a network of metal or plastic fibers.

Figure 5:
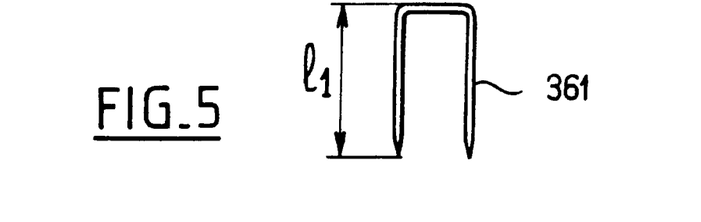
FIG. 5 is an enlarged diagram of a binding staple, in its original state.
Figure 6:
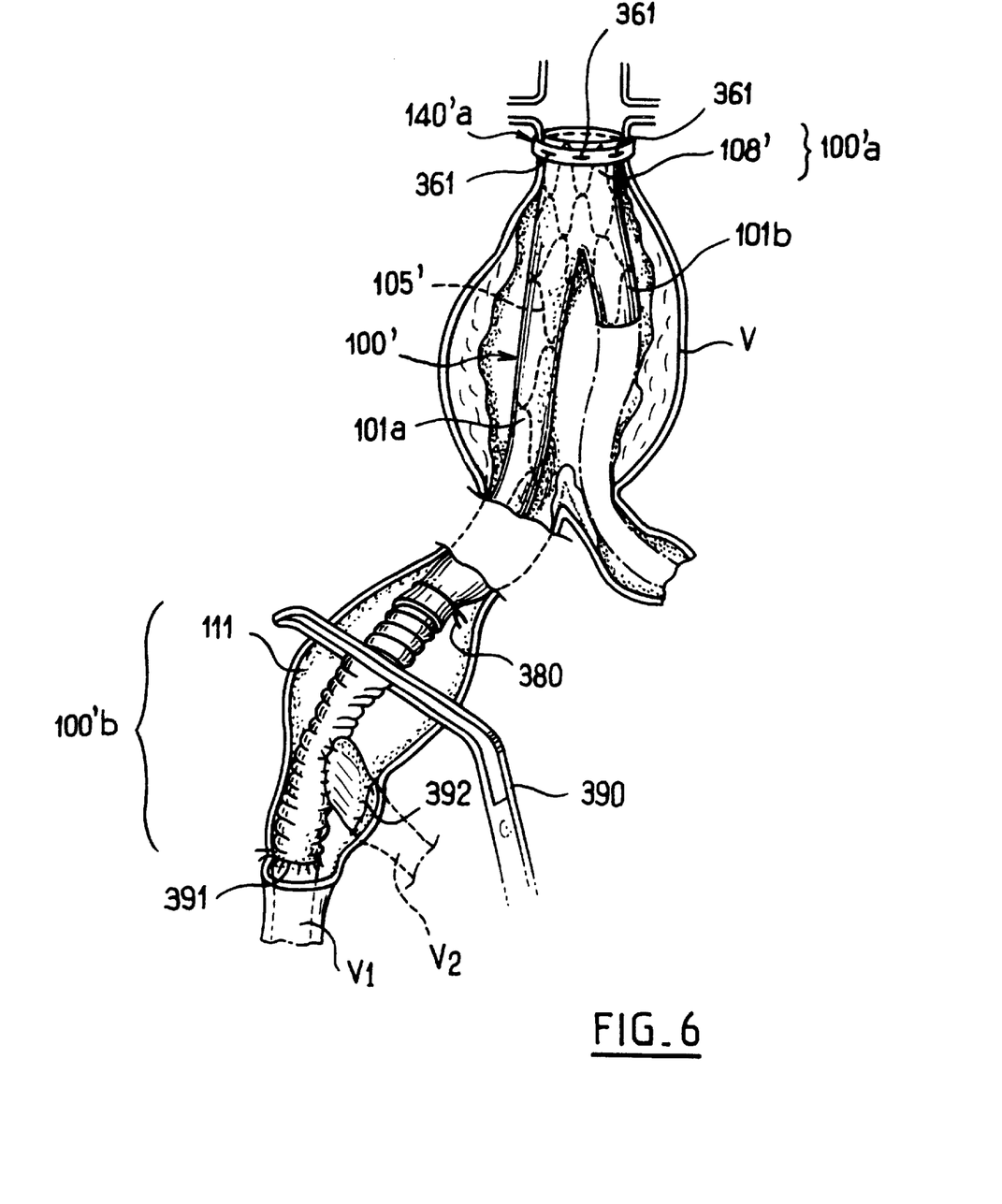
FIG. 6 is a diagram (on a smaller scale) of the setting of a variation in the implementation of the implant of FIG. 1, with a single lining.
Figure 9:
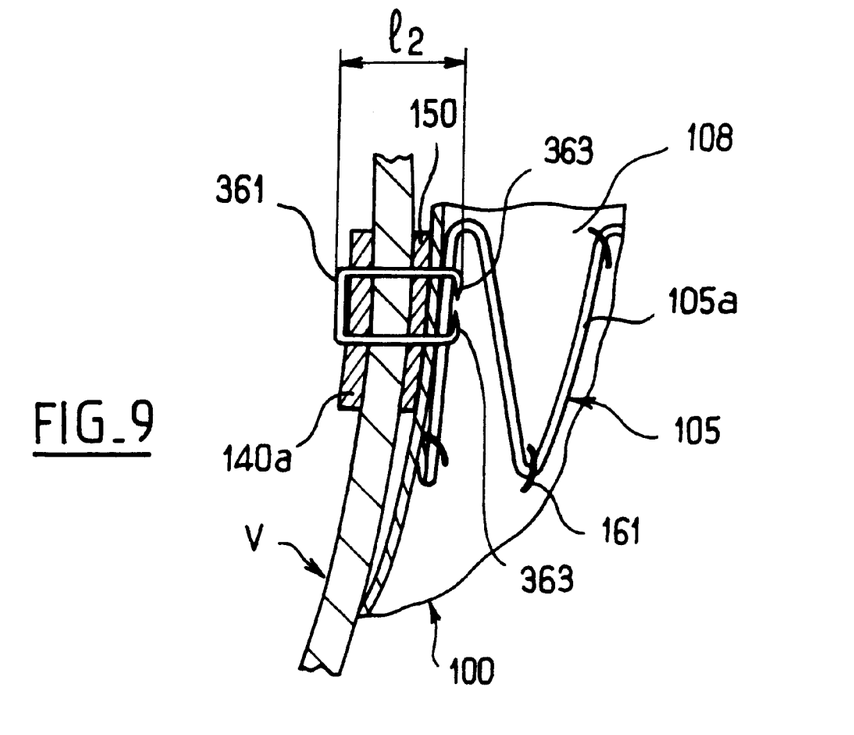
FIG. 9 shows, enlarged, a local area of a fastened implant, with a staple tightened against the implant.

The solution adopted in FIG. 3 for these fastening means or the one using reinforced felt are particularly suitable to a binding by stitches (surgical stitches) between the strap and the implant 100, the practitioner working then from the outside of the vessel (through endoscopy or after stripping) while the solution in FIG. 2 may be particularly suitable if the fastening is done by "staples," as illustrated in particular in FIGS. 5, 6 and 9, or by "rivets" as in FR 97 16625.

Were the fastening means liable to penetrate too forcefully the strap and/or the sleeve 108 of the prosthesis, then one and/or the other of these two pieces could be designed with openings such as cut-outs made in the shape, for instance, of crosses or partial circles, as represented in 319 on FIG. 2. It is to be noted that the size of the mesh 309a of the lattice of FIG. 3 can have the same effect.

Figure 4:
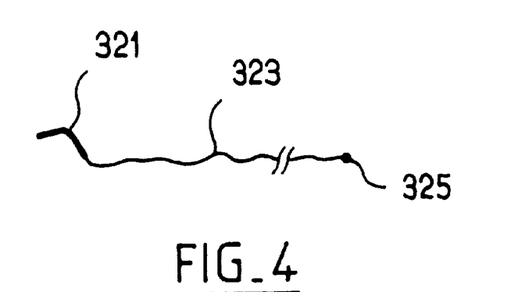
FIG. 4 shows a threaded needle ready for stitching (off scale)

In FIG. 4, we have a diagram of a curved stitching needle 321 with its suturing thread 323 used to bind together the prosthesis and the lining strap, through the vessel wall. The thread 323 ends with a knot 325 to hold the thread in place, once inserted.

In FIG. 5, a diagram of a surgical fixation staple 361 having a "⊔" shape is illustrated.

In FIG. 6, a diagram of a variation of the case represented in FIG. 1 is shown. Here the implant 100' is meant to be locally affixed and tightly pressed against the duct V through a single collar or thong 140'a, at its proximal end 100'a. The distal end 100'b is located in the area of the lower neck of the lower aneurysm 111, near the junction between the iliac vessel V1 and the hypogastric artery V2. The implant 100' is devoid of anchoring hooks (even though these were very often used prior to this invention.)

The implant 100' comprises a proximal part in the shape of a "Y" with an upper common trunk and two lower branches 101a, 101b. The branch 101a is longer than the other that itself ends in the aortic aneurysm (prior to being attached to a connecting implant not shown here and represented by dotted lines).

The implant 100' comprises a sleeve 108' made of fabric and supported by a structure made of layered "stents," present inside the sleeve except in the most distal part 100'*b* where this sleeve is, on some of its length (a few centimeters) devoid of any mechanical support structure, as described in WO-A-97/41804 introduced in the description by reference.

Figure 7:
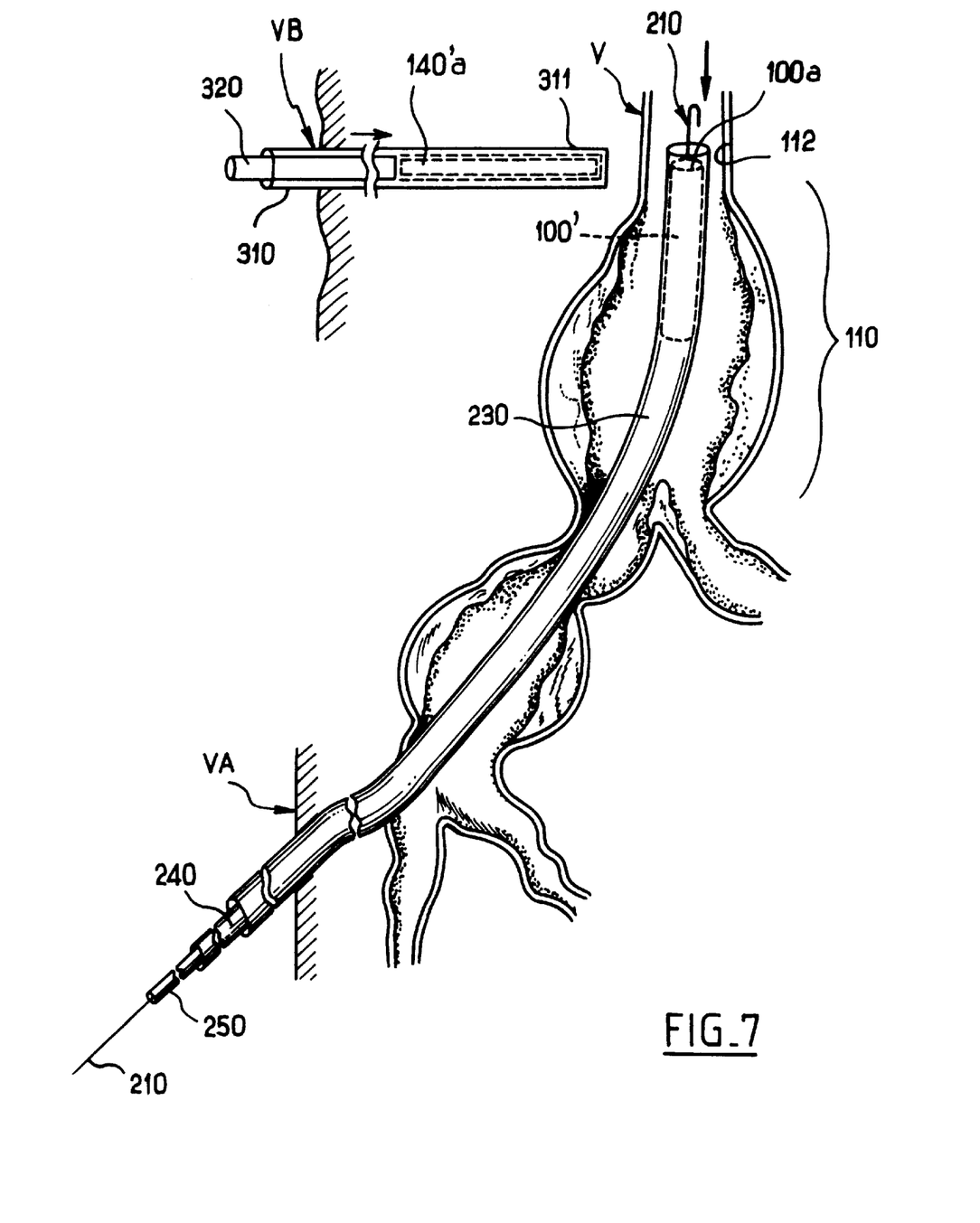
FIG. 7 shows an implantation step prior to the situation depicted in FIG. 6.

FIG. 7 is a diagram of a technique for the implantation of the endoprosthesis 100', through an endoluminal percutaneous access (the "SELDINGER" technique, in particular), as well as of the setting of the collar 140'*a*, preferably by laparoscopic access.

More precisely, once an access VA is made through the patient's skin and a stretching or dilating catheter (not represented) is introduced on the thread-guide 210, the outer sheath 230, containing a second sheath 240 the thread-guide 210, the outer sheath 230, containing a second sheath 240 near the distal end where the implant 100' was already preloaded, is introduced, after the means of dilation are taken out.

Upon reaching the area 110 (upstream) of the aortic aneurysm, the proximal end of the implant is suitably positioned, by radiographic means.

Both sheaths 230, 240 are then successively withdrawn, the inner catheter 250 supporting, if need be, the rear of the implant, so as to avoid a possible backlash when the sheaths are withdrawn The implant 100' then unfolds radially, on its own if it is self-expansible or else due to a predesigned inner means of inflation, or by any other suitable means.

Once the implant unfolded, a sheath 310 containing the lining 140'*a* is introduced by laparoscopic means (endoscopy) essentially at the level of the upstream neck 112 of the aneurysm, across the vessel axis and thus the implant, through the percutaneous access VB performed here in the abdominal area.

Once the distal end 311 of the sheath 310 essentially faces the implant end 100'*a*, the sheath is withdrawn, using again for rear support a catheter 320 on which will rest the collar 140'*a* that may have been, for its introduction, stretched flat in the sheath, at the end of the "trigger" 320.

If the lining 140'*a* is a strap that can close itself in the shape of a split ring, as shown in FIG. 1, a progressive release will allow it to naturally come around the neck 112. Otherwise, and in particular if the structure of the lining is not susceptible to elastic distortion, the introduction (still by laparoscopic means, though stripping is always an option) of one or more pliers should allow the practitioner to mold the strap 140'*a* to the local outer area 112, into the shape of a split ring. The strap distortability, that may be comprised between about 2 to 6 cm. in length, and between 0.5 mm. and a few millimeters in width, makes its shaping easier.

If the lining is provided with an extra-length as a security measure (see FIG. 11), it will then be cut (to the appropriate length).

If this lining is fastened by stitching (see FIG. 4), then pliers can be used to work the needle 321 (also previously introduced by laparoscopic access inside a catheter or an insertion sheath), until the practitioner can pull the thread 323 several times through the strap 140'*a*, the vessel area 112 and the implant area 100*a*, surrounding at least part of the vessel. Preferably this thread will be slipped behind the corresponding stent and/or through the ring supporting the implant if provided (reference 150 in FIG. 1), which could be located on the outside of the implant as shown in FIG. 9. It is also possible to design instead a single pad, made for instance of bio-compatible felt coated on the outside with silicone and fastened to the endoprosthesis.

Figure 8:
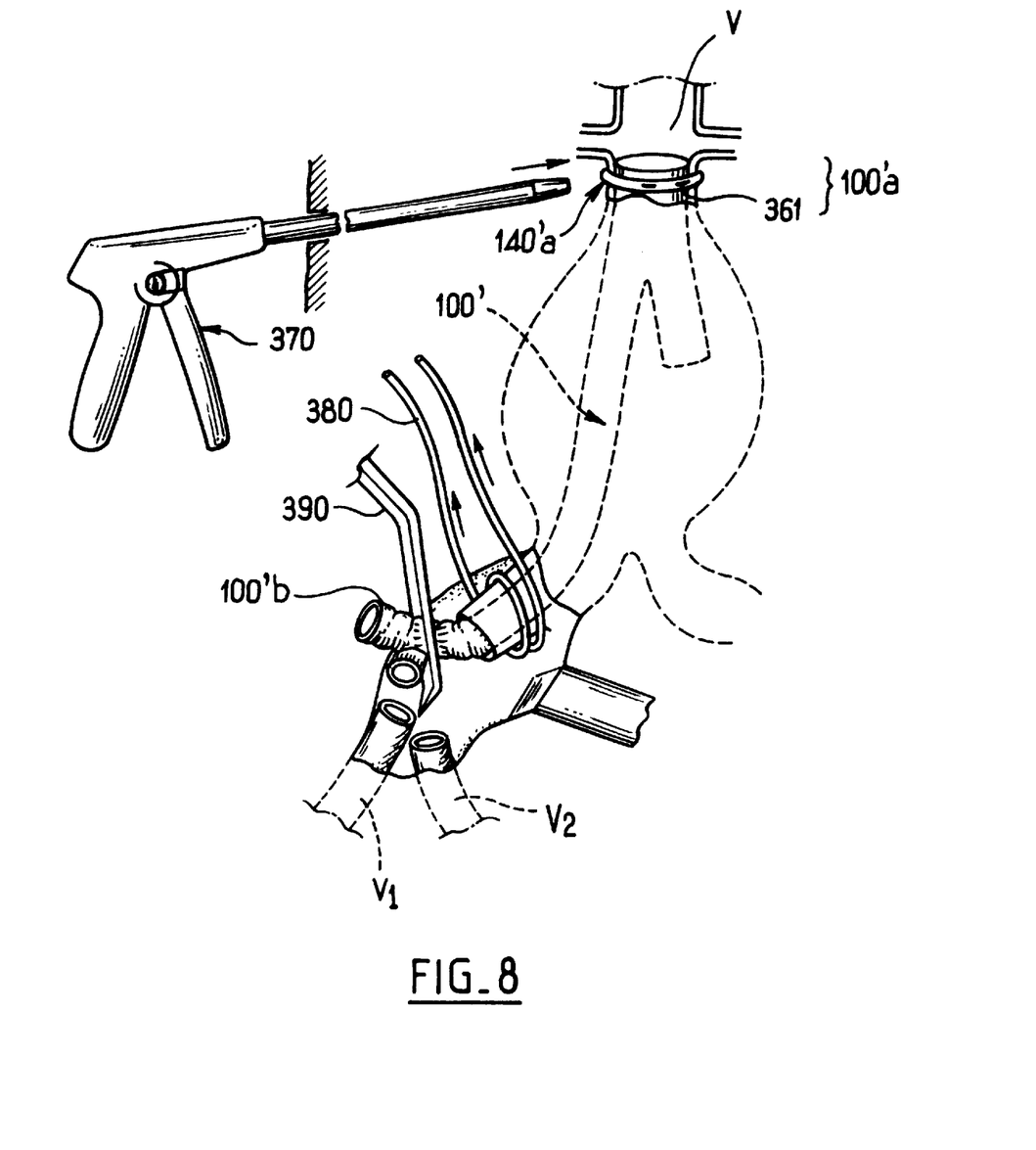
FIG. 8 shows an intermediate implementation step between the situations shown in FIGS. 6 and 7.

The stitch will preferably be tightened from the outside of the vessel, so as to closely affix the part 100'*a* of the implant against the inner surface of the neck 112, thus insuring a bloodproof environment The same preference applies if the fastening is done by staples such as 361, as shown in FIGS. 5, 8 and 9, the folding area 363 of the free ends of each staple providing an effective holding.

FIG. 8 is a diagram showing precisely how the stapling of the proximal end 100'*a* of the implant could be implemented before the distal end 100'*b* is fastened surgically.

The type of stapler and staples will be described in more detail thereafter. However, it is already to be noted that it is possible to use a stapler 370 introduced by endoscopy up to the outer duct wall and loaded with staples such as 361 (FIG. 5), these staples being distorted into the tight fastened shape shown in FIG. 9.

Once a series of staples fastened at the periphery of the collar 140'*a*, essentially perpendicular to the duct axis, the practitioner will proceed to fasten the downstream area 100'*b* of the implant, as shown in WO-A-97/41804. The area surrounding the lower aneurysm 111 was already stripped and the appropriate ligatures and pincings (such as sketchily represented in 380, 390 in FIG. 8) were implemented.

He then grabs the loose end 100'*b* that he cuts to the desired length.

Next, he surgically connects this cut end to the vessel(s) (for instance, with stitches such as 391, 392 in FIG. 6), while passing through the sheath 108 and the vessel wall.

Of course, if two vessels must be rechanneled (V1, V2), the end 100'*b* is branched, as shown in FIGS. 6 and 8.

To set and hold the possible connecting implant shown in dotted lines in FIG. 6, the practitioner may then proceed as shown in ways already known prior to this invention.

Once all the instruments and means of implantation taken out, the access routes are closed.

As a duct other than a blood vessel that could benefit from the technique of this invention, the gall bladder may be mentioned (see WO-A-97/09008 for dimensions/size, materials, . . . , cf pages 8 to 11 in particular).

Alternatively, the endoprosthesis 100 could be in the shape of a branched tube, as in U.S. Pat. No. 5,527,355.

Other types of endoluminal implants could also be suitable.

Figure 10:
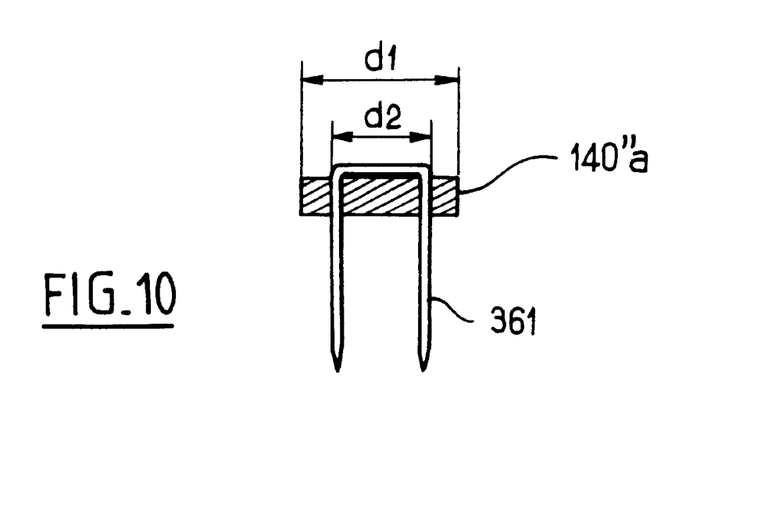
FIG. 10 shows a staple in its original state, crossing a fluidtight pad.

In FIG. 10, the outer lining of the duct was referenced as 140"*a*. It is shown as a round piece (disk) but can have any other desired shape (rectangular, in particular). Its structure can be made of felt, silicone or, more generally, of the same material as the strap 140*a* already described.

Figure 11:
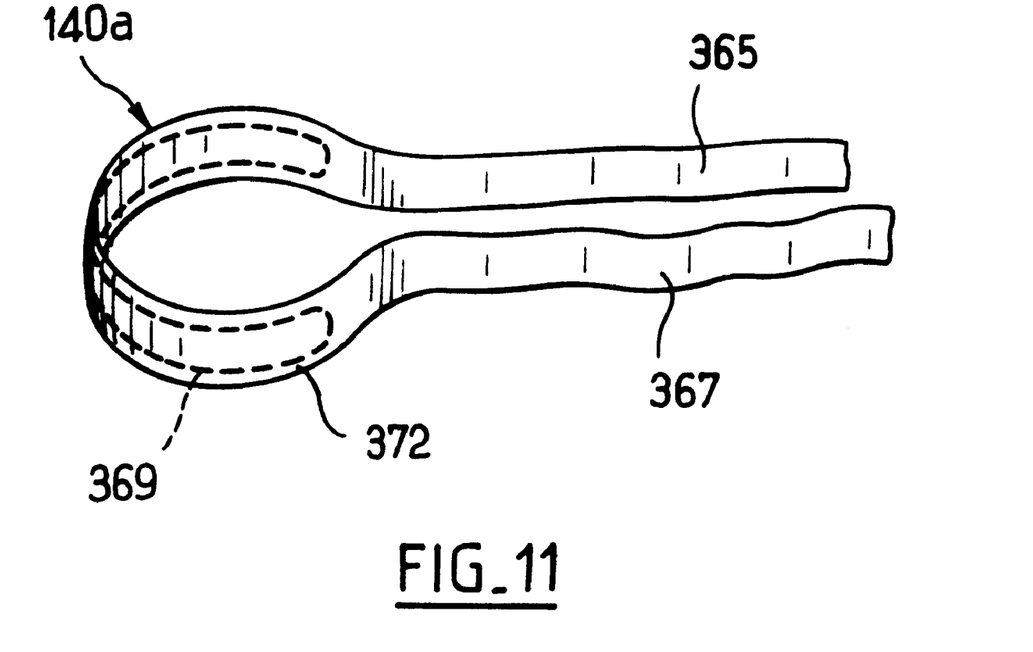
FIG. 11 shows, on a larger scale than FIG. 1, a possible implementation of a fastening lining.

The diameter (or width) d1 of this pad is a few millimeters or centimeters larger than the width d2 of the staple 361, so as to then replace the strap, with, in this case an outer overlap more localized of the given duct To fasten the endoprosthesis of FIG. 1, it is recommended to proceed as follows:

The setting of the implant 100 can be implemented as that of the implant 100', and the same goes for the setting of the collar 140*a* (see setting collar 140'*a*). If the collar is as shown in FIG. 11, with a bloodtight strap extending to 365, 367 beyond a central area that presents a reinforcing core 369 in the shape of a split ring, elastically distortable radially, an adjustment of the length of the collar 140*a* will be implemented if need be by cutting the extensions 365, 367 (made of fabric, such as DACRON®).

The setting and adjusting of the "downstream" collar 140*b* is done likewise, except that the implant was then already fully released in the vessel V, since it is only present in the area of the aneurysm 110.

Figure 12:
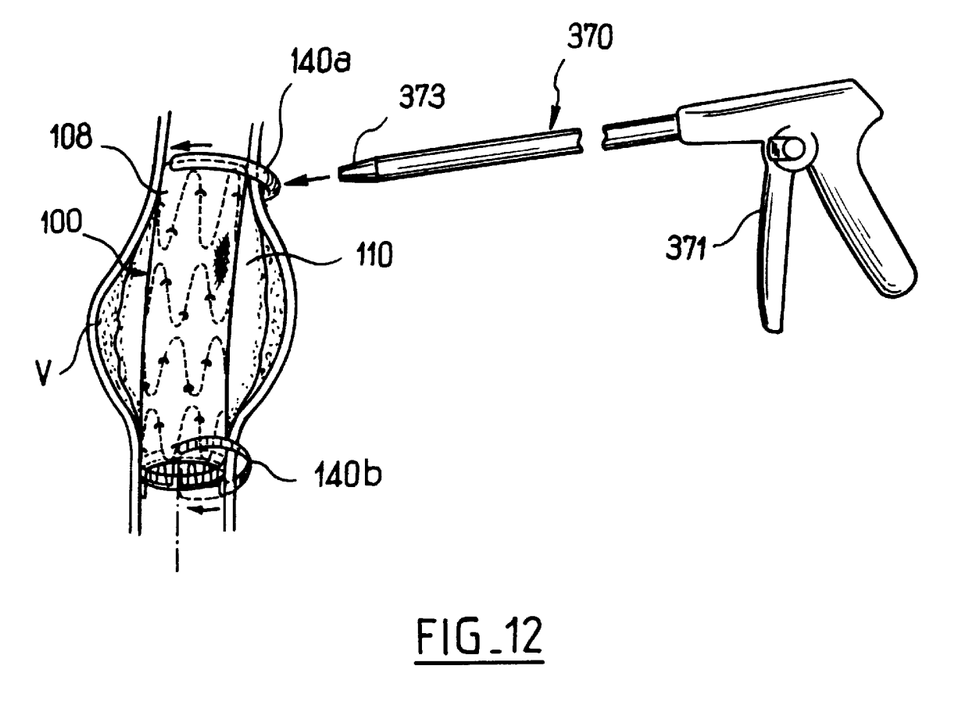
FIG. 12 is a small-scale diagram of the setting and stapling of the linings for an implant such as illustrated in FIG. 1.

To then fasten together each collar/the vessel/the implant, in particular by a series of staples 361, the practitioner can use an endoscopic stapler such as described in U.S. Pat. Nos. 5,246,156, 5,333,772, 5,470,010 or else of the model <<ENDOPATH EMS® from the corporation ETHICON, CINCINNATI, Ohio, USA>>, which allows for one-sided stapling. Besides, and whether endoscopic or not, this type of unilateral stapler, referenced as 370 in FIG. 12, is loaded with staples in the original shape "⊓" as shown on FIG. 5. After the tip 373 of the stapler is placed against the outer surface of the collar, the action of the release trigger 371 first drives a staple through the aforementioned layers (while maintaining its original shape essentially in "⊓"), and then, at the end of its stroke closes the staple ends in the desired shape of a "⊏⊐" to reach the situation shown in FIG. 9 in which the collar, the vessel V and the implant are tightened together. Between these two shapes, the length (l1, then l2). of the staple was thus reduced to promote the tightening and a bloodproof fastening.

It is worth noting that this variation in length of the fastening means would also occur if rivets such as described in FR 97 16625 were used instead of staples.

The bloodtightness on the outside of the vessel should be achieved by using a self-obturating coat 372 (made of silicone, for instance; FIG. 11) on each collar. Inside, if there is still a risk, the intermediary pad 150 of FIG. 9 provides a solution. But then the means of transvascular fastening must go through an additional thickness. Another solution consists in coating on the outside with a layer of self-obturating material at least the proximal and/or distal ends of the implant casing (see areas 395 and 397 in FIG. 1).

Of course, to thus insure a bloodtight fastening of the collars, the practitioner will have had to perform several series of transcutaneous incisions, if an endoscopic approach was chosen over a vascular stripping.

Figure 13:
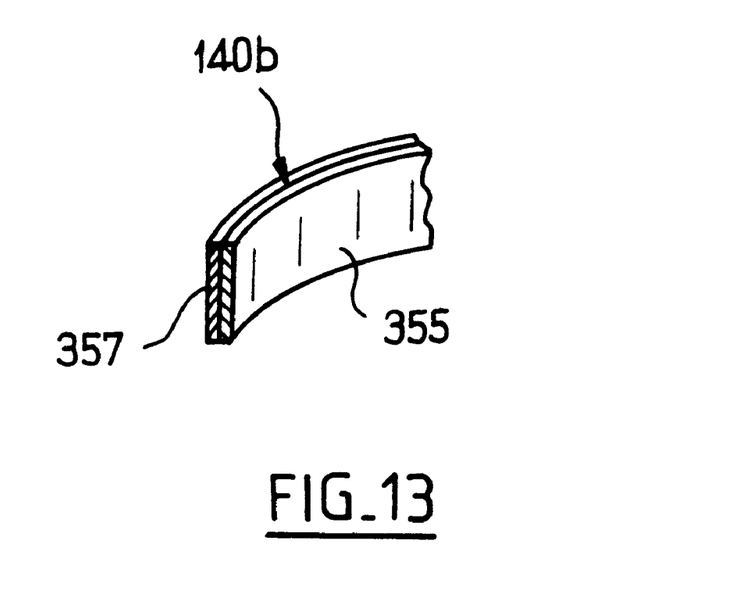
FIG. 13 shows a local view of a possible implementation of the lining.

FIG. 13 shows a part of a lining referenced as 140b. It is characterized in that its inner surface 355 (destined to come in contact with the duct V) is made of an "adhesive" material or one that enhances the adhesion to the duct, such as a material favorable to cellular growth, a polyester or a TEFLON® foam for instance. On the other hand, its outer surface 357 is in "non-adhesive" material or, more accurately, a material such as a silicone, not susceptible to adhere to an anatomic part and in particular not favorable to cellular growth on contact The lining 140b may comprise two layers 355, 357 as in FIG. 13, with, for instance, a silicone tongue on the outside and a polyester pad on the inside, or else a central core (for mechanical reasons) coated respectively on the inside and on the outside with two films 355, 357. Conversely, the strap 150 may be designed with outer "adhesion," on the side facing the duct and, if necessary, inner "non-adhesion."

What is claimed is:

1. A medical device for treating an affection of an anatomical duct, the device comprising:
    an intraluminal tubular prosthesis adapted to be inserted in the duct, the prosthesis having a first end and a second end, and comprising a sleeve for canalising a corporal fluid therethrough,
    a strap adapted to be disposed adjacent one of the first and the second ends of the prosthesis on an outer surface of the duct, and
    fastening means for passing through the strap, a wall of the duct and the sleeve of the prosthesis, from outside the duct towards the prosthesis disposed therein, for fixing them all together, the fastening means adapted to be deformed and having a length sufficient to pass through the strap, the duct wall and the prosthesis to effect a fluid-tight seal upon deforming said fastening means,
    the strap comprising:
        a strengthening structure having a split ring shape, and
        a self sealing member extending along the strengthening structure and adapted for being sealingly passed through by said fastening means.

2. The device according to claim 1, wherein the strap comprises a first and a second end, and divisible portions at said first and second ends, the strap being longer in length than a perimeter of the duct, and the divisible portions being adapted to be cut to length as a function of the perimeter of the duct.

3. A medical device for treating an affection of an anatomical duct, the device comprising:
    an intraluminal tubular prosthesis adapted to be inserted in the duct, the prosthesis having a first end and a second end,
    a strap adapted to be disposed adjacent one of the first and the second ends of the prosthesis on an outer surface of the duct,
    fastening means for passing through the strap, a wall of the duct and the prosthesis, for fixing them all together, the fastening means comprising surgical staples, the staples being adapted to be deformed and having a length sufficient to pass through the strap, the duct wall and the prosthesis to effect a fluid-tight seal upon deforming the staples, and
    a surgical stapler adapted for introducing, from outside the duct, said surgical staples through the strap, the duct wall and the prosthesis, and for deforming said staples to effect a fluid-tight connection between the strap, the duct wall and the prosthesis.

4. A medical device for treating an affection of an anatomical duct, the device comprising:
    an intraluminal tubular prosthesis adapted to be inserted in the duct, the prosthesis having a first end and a second end,
    a strap adapted to be disposed adjacent one of the first and the second ends of the prosthesis on an outer surface of the duct, and
    fastening means for passing through the strap, a wall of the duct and the prosthesis, from outside the duct towards the prosthesis disposed therein, for fixing them all together, the fastening means adapted to be deformed and having a length sufficient to pass through the strap, the duct wall and the prosthesis to effect a fluid-tight seal upon deforming said fastening means, the fastening means having an axis, a first length along the axis, when passing successively through the strap, the duct and the prosthesis, and a second length along said axis, when effecting upon deformation the fluid-tight seal, the second length being less than the first length.

5. The device according to claim 4, wherein the fastening means comprise surgical staples, the staples adapted to be deformed and having a length sufficient to pass through the strap, the duct wall and the prosthesis to effect a fluid-tight seal upon deforming the staples.

6. The device according to claim 5, further comprising a surgical stapler adapted for introducing, from outside the duct, said surgical staple through the strap, the duct wall and the prosthesis, and for deforming said staple to effect a fluid-tight connection between the strap, the duct wall and the prosthesis.

7. A medical device for treating an affection of an anatomical duct, the device comprising:
   an intraluminal tubular prosthesis adapted to be inserted in the duct, the prosthesis having a first end and a second end, and comprising a sleeve for canalising a corporal fluid there through,
   a strap adapted to be disposed adjacent one of the first and the second ends of the prosthesis on an outer surface of the duct, and
   fastening means for passing through the strap, a wall of the duct and the sleeve of the prosthesis, for fixing them all together, the fastening means being adapted to be deformed and having a length sufficient to pass through the strap, the duct wall and the prosthesis to effect a fluid-tight seal upon deforming said fastening means, the fastening means having an axis, a first length along the axis, when passing through the strap, the duct and the prosthesis, and a second length along said axis, when effecting upon deformation the fluid-tight seal, the second length being less than the first length.

* * * * *